US012778607B2

(12) United States Patent
Garcia

(10) Patent No.: US 12,778,607 B2
(45) Date of Patent: Nov. 3, 2026

(54) OSTEOTOMY JIG

(71) Applicant: Nicholas Robert Garcia, Shaker Heights, OH (US)

(72) Inventor: Nicholas Robert Garcia, Shaker Heights, OH (US)

( * ) Notice: Subject to any disclaimer, the term of this patent is extended or adjusted under 35 U.S.C. 154(b) by 1 day.

(21) Appl. No.: 19/059,776

(22) Filed: Feb. 21, 2025

(65) Prior Publication Data

US 2026/0248519 A1 Aug. 27, 2026

(51) Int. Cl.

*A61B 17/17* (2006.01)
*A61B 17/15* (2006.01)
*A61B 17/88* (2006.01)

(52) U.S. Cl.

CPC ........ *A61B 17/1775* (2016.11); *A61B 17/151* (2013.01); *A61B 17/8897* (2013.01)

(58) Field of Classification Search

CPC . A61B 17/1697; A61B 17/17; A61B 17/1714; A61B 17/1775; A61B 17/1796; A61B 17/6416; A61B 17/6433; A61B 17/848; A61B 17/8897; A61B 17/90; A61F 2/4606

See application file for complete search history.

(56) References Cited

U.S. PATENT DOCUMENTS 11,229,443 B2 * 1/2022 Wong ............... A61B 17/00234

* cited by examiner

*Primary Examiner* — Larry E Waggle, Jr.

(74) *Attorney, Agent, or Firm* — Brennan, Manna & Diamond, LLC

(57) ABSTRACT

An osteotomy jig for performing a minimally invasive surgical correction of a Tailor's bunion. A first and second j-arm are nested within a burr collar on opposite sides and extend in opposing directions. The first j-arm is configured to position an intersecting wire pin along a long axis of the fifth metatarsal. The first j-arm, the second j-arm and the burr collar are each configured to position a lynch pin perpendicularly to the intersecting wire pin. An osteotomy is performed through a burr opening in the burr collar proximal to and parallel with the lynch pin wire. The second j-arm is configured to orient a throw wire after translation angled to intersect the lynch pin and the intersecting wire to complete a temporary fixation prior to placing a bone screw for permanent fixation.

19 Claims, 6 Drawing Sheets

OSTEOTOMY JIG

FIELD OF THE INVENTION

The present invention generally relates to a medical device for use in the field of minimally invasive foot and ankle surgery. More particularly, the present invention relates to an osteotomy guide used in a minimally invasive surgical correction of a Tailor's bunion that is configured to help provide a temporary fixation prior to the placement of a bone screw after performance of an osteotomy. Accordingly, the present specification makes specific reference thereto. However, it is to be appreciated that aspects of the present invention are also equally amenable to other like applications, devices, and methods of manufacture.

BACKGROUND

Minimally invasive surgical procedures encompass surgical techniques that limit the size of incisions needed. Surgery by definition is invasive, and many operations requiring incisions of some size are referred to as open surgery. Incisions made during open surgery can sometimes leave large wounds that may be painful and take a long time to heal. Foot and ankle orthopedic surgeons use minimally invasive surgery (MIS) to correct specific foot and ankle conditions with very small incisions. One common condition that can be treated using minimally invasive surgical techniques is a bunion.

Bunions occur when the bones in the front of the foot move out of place, causing the big toe to point toward the smaller toes. Bunions cause pain, stiffness, swelling, discoloration, loss of flexibility, and numbness. A bunion, or a hallux valgus, is a bony bump that forms on the joint at the base of the big toe known as the metatarsophalangeal (MTP) joint. A bunionette, or Tailor's bunion, is a bony deformity that affects the MTP joint at the base of the little toe. It is characterized by a painful bump on the outside of the foot, near the fifth metatarsal bone. They affect between 13.8 and 23 percent of the population and co-present with an additional deformity in approximately 60 percent of patients.

The rise of minimally invasive foot and ankle surgery has afforded percutaneous instrumentation that facilitates classical techniques, minimized dissection and preservation of adjacent soft tissues, and an expanded patient demographic for providers. It has also increased cosmesis, provided same-day weight bearing, lowered post-operative pain scores, and decreased post-operative narcotic use for patients.

However, the widespread adoption of MIS for treating bunionettes has encountered a variety of challenges, such as, a lack of instruction across residency and fellowship training, a lack of universally accepted standards for practice, no guiding authority, patient demand that exceeds the pool of trained providers, and a steep learning curve. One current market option is a stemmed linear implant. However, this is ineffective when the patient has a curvilinear metatarsal shaft. Another option is a floating osteotomy. However, this can lead to hypertrophic non-unions in active patients and atrophic non-unions in osteopenia or medically comorbid patients. There is currently no ideal option available to treat all three subtypes of pathology that can present with a Tailor's bunion.

Accordingly, there is a great need for guided instrumentation that can lower the threshold for provider entry into MIS for treating Tailor's bunions. There is also a need for guided instrumentation that can increase procedure consistency and reproducibility. Similarly, there is a need for a device that provides a minimally invasive option for correcting a Tailor's bunion as opposed to performing a traditional open surgical procedure. There is also a need for a surgical option that avoids the pit-falls of free floating osteotomies. Further, there is a need for a surgical option that allows for a doctor's office based hardware removal.

In this manner, the improved osteotomy jig of the present invention accomplishes all of the forgoing objectives, thereby providing an easy solution for lowering the threshold for provider entry into MIS for treating Tailor's bunions. A primary feature of the present invention is an osteotomy jig that can increase procedure consistency and reproducibility in surgical outcomes. The present invention allows for a two stitch alternative to an open surgical correction. Finally, the improved osteotomy jig of the present invention is capable of avoids the pit-falls of free floating osteotomies, accelerating recovery, and allowing for same day weight bearing post procedure.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The subject matter disclosed and claimed herein, in one embodiment thereof, comprises an osteotomy jig for a surgical repair of a Tailor's bunion. The osteotomy jig comprises a first arm, a burr collar component, and a second arm. The first arm comprises a distal portion, an extension portion, and a proximal portion. The distal portion curves out of the extension portion and terminates in an intersecting wire guide that is parallelly oriented to the extension portion. The intersecting wire guide is sized to accept passage of a K-wire. The proximal portion comprises a medial side for positioning adjacent to a head of the fifth metatarsal, and a lateral side comprising a nesting portion. The proximal portion further comprises a lynch pin guide penetrating the proximal portion from the medial side through the lateral side.

The burr collar component comprises a nesting portion and a burr guide extension. The nesting portion comprises a medial side collar and a lateral side collar. The medical side collar is configured to accept the nesting portion of the lateral side of the proximal portion of the first arm to rotatably connect the burr collar component and the first arm. The nesting portion of the burr collar component further comprises a lynch pin guide. The lynch pin guide of the burr collar component is sized and oriented to align with the lynch pin guide of the first arm to accept passage of a K-wire. The burr guide extension extends from the nesting portion and comprises a burr opening.

The second arm comprises a distal portion, an extension portion, and a proximal portion. The distal portion comprises a medial side and a lateral side comprising a nesting portion. The distal portion further comprises a lynch pin guide penetrating the proximal portion from the medial side through the lateral side. The lynch pin guide of the second arm is sized and oriented to align with the lynch pin guides of the first arm and the burr collar component to accept passage of a K-wire. The proximal portion curves out of the extension portion and terminates in a throw wire guide that is angled with respect to the extension portion. The throw wire guide is sized to accept passage of a K-wire.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION

Figure 1:
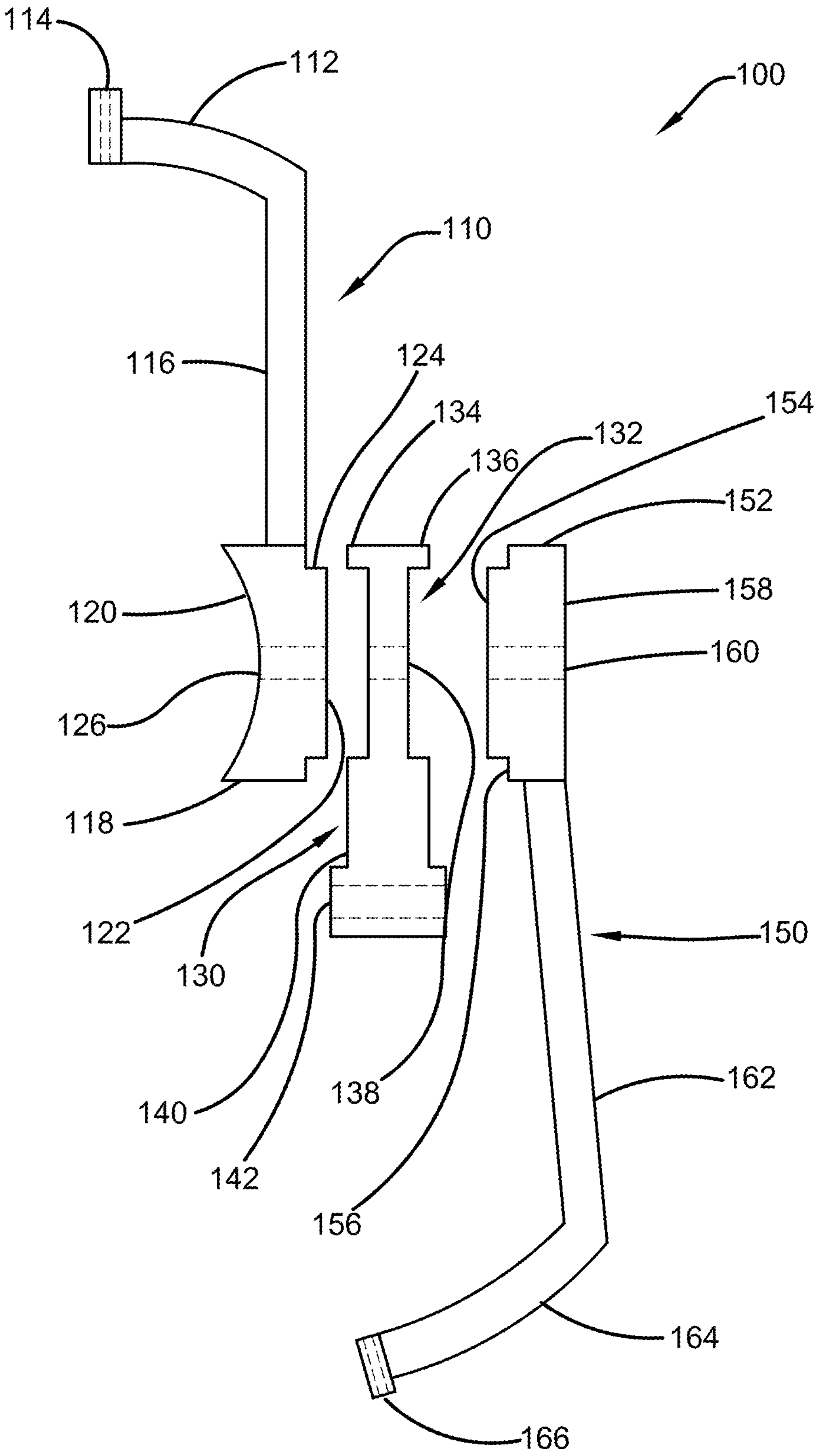
FIG. 1 illustrates an exploded perspective view of an osteotomy jig of the present invention for a surgical repair of a Tailor's bunion in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They do not intend as an exhaustive description of the invention or do not limit the scope of the invention. Additionally, an illustrated embodiment need not have all the aspects or advantages shown. Thus, in other embodiments, any of the features described herein from different embodiments may be combined.

The present invention, in one exemplary embodiment, is an osteotomy jig configured to assist a surgeon in a surgical repair of a Tailor's bunion. The osteotomy jig is configured to guide the position of wires to temporarily fix a translated fifth metatarsal bone post osteotomy in a corrected anatomical position prior to permanent fixation. A first and second j-arm are nested within a burr collar on opposite sides extending in opposing directions. The first j-arm is configured to position an intersecting wire along a long axis of the fifth metatarsal. The first j-arm, the second j-arm and the burr collar are each configured to position a lynch pin perpendicularly to the intersecting wire. The burr collar is configured to allow an osteotomy to be performed through a burr opening in the burr collar proximal to and parallel with the lynch pin wire. The second j-arm is configured to orient a throw wire after translation angled to intersect the lynch pin and the intersecting wire to complete a temporary fixation prior to placing a bone screw for permanent fixation.

Figure 2:
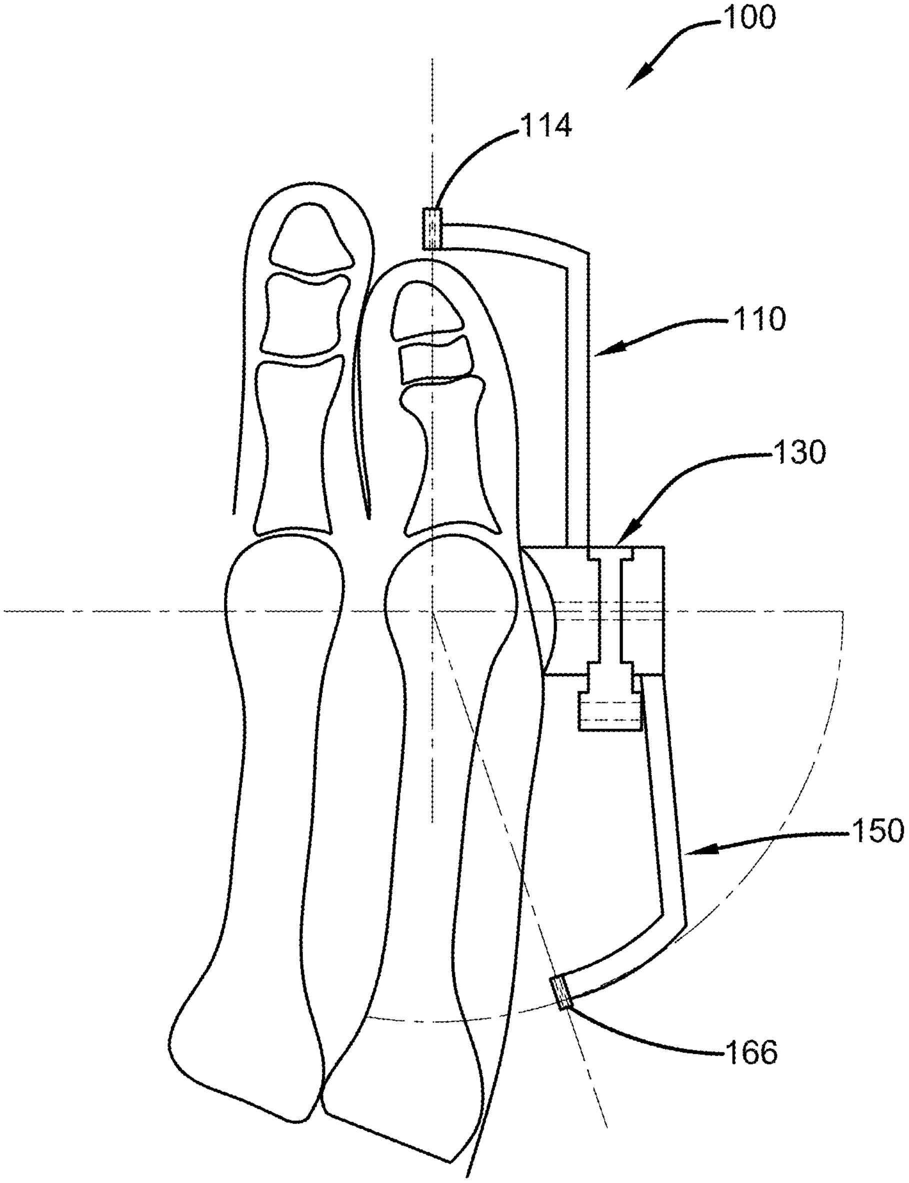
FIG. 2 illustrates a perspective side view of the osteotomy jig of the present invention positioned for a surgical repair of a Tailor's bunion in accordance with the disclosed architecture.
Figure 3:
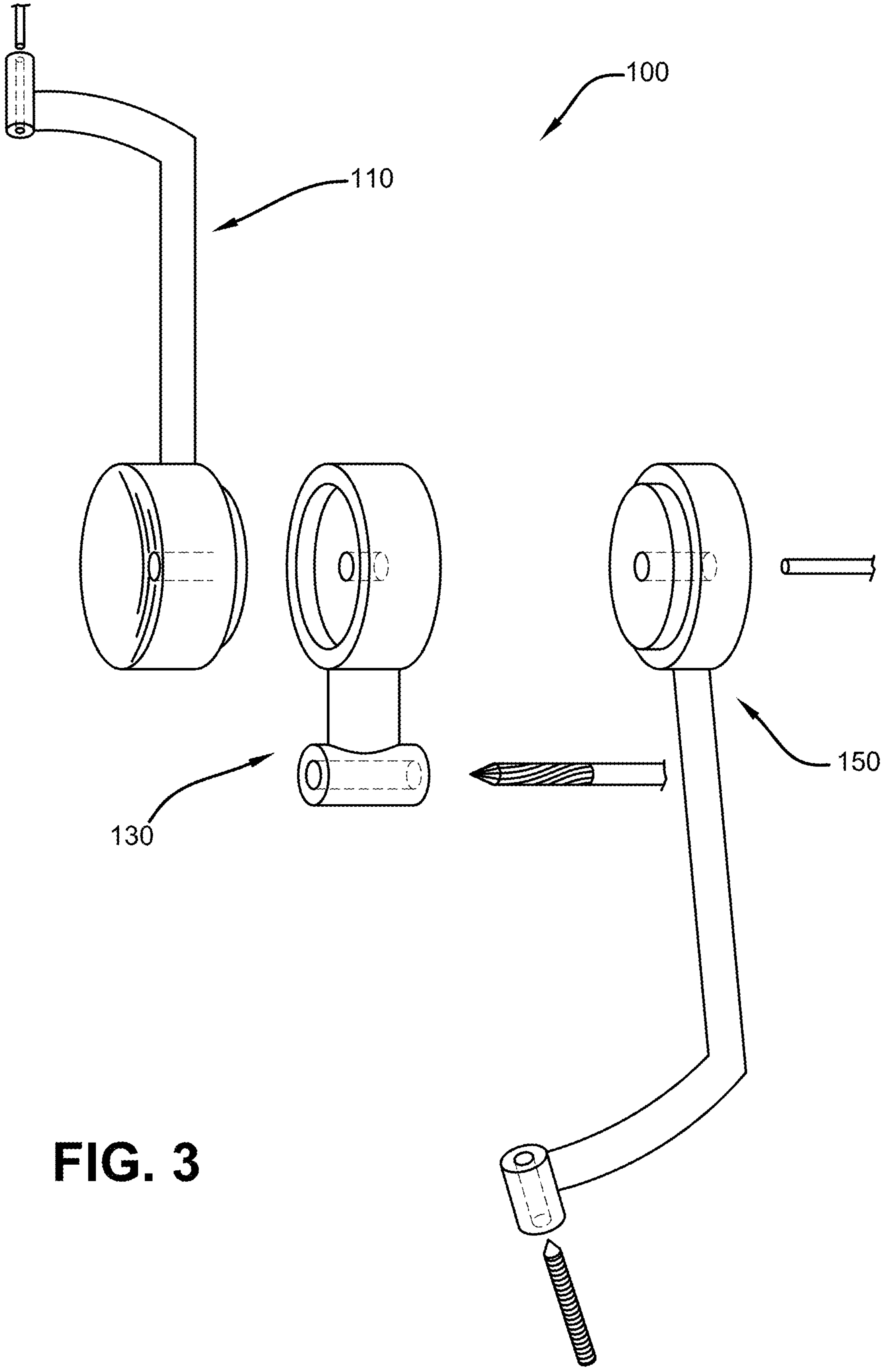
FIG. 3 illustrates an exploded perspective view of the osteotomy jig of the present invention for a surgical repair of a Tailor's bunion in accordance with the disclosed architecture.

Referring initially to the drawings, FIG. 1-3 illustrates an osteotomy jig 100 for a surgical repair of a Tailor's bunion. The osteotomy jig 100 is a Tailor's bunion correction device which allows the surgeon to control the fifth metatarsal head while performing an osteotomy and bunion correction procedure. The osteotomy jig 100 is used in conjunction with MIS procedures and comprises a first arm, 110 a burr collar component 130, and a second arm 150. The osteotomy jig 100 can be manufactured of stainless steel, titanium, polyether-ether-ketone, polymers, plastic, or any other biocompatible material as is known in the art.

Further, the first arm, 110 the burr collar component 130, and the second arm 150 can be any suitable size, shape and configuration as is known in the art without affecting the overall concept of the invention. One of ordinary skill in the art will appreciate that the shape and size of the first arm, 110 the burr collar component 130, and the second arm 150 as shown in FIGS. 1-3 is for illustrative purposes only and many other shapes and sizes of the first arm, 110 the burr collar component 130, and the second arm 150 are well within the scope of the present disclosure. Although dimensions of the first arm, 110 the burr collar component 130, and the second arm 150 (i.e., length, width, and height) are important design parameters for good performance, the first arm, 110 the burr collar component 130, and the second arm 150 may be any shape or size that ensures optimal performance during use, and may even be customized to fit the exact specifications/measurements of the patient's fifth metatarsal. As such, the osteotomy jig 100 may be comprised of sizing/shaping that is appropriate and specific in regard to whatever the osteotomy jig 100 is designed to be applied.

The first arm 100 comprises a distal portion 112, an extension portion 116, and a proximal portion 118. The distal portion 112 forms a j-arm that curves out of the extension portion 116. The distal portion 112 terminates in an intersecting wire guide 114. The intersecting wire guide 114 is generally parallelly oriented to the extension portion 116 extending back toward the proximal portion 118. The intersecting wire guide 114 is cylindrical in shape and canulated and sized to accept passage of a K-wire or similar pin for temporary fixation. Typically, the intersecting wire guide 114 is sized to accept a 0.045 inch diameter K-wire, although it can be sized to accept larger or smaller diameters as needed depending on the size of the patient. When the first arm 110 is in position, the intersecting wire guide 114 is anatomically oriented to position a K-wire parallel to a long axis of the fifth metatarsal to allow a uniform translation of the fifth MPJ joint.

The proximal portion 118 comprises a medial side 120 for positioning adjacent to a head of the fifth metatarsal. The proximal portion 118 may be cupped to better fit a patient's anatomy. The proximal portion 118 further comprises a lateral side 122. The lateral side 122 comprises a nesting portion 124. The nesting portion 124 is configured to engage the burr collar component 130 as described infra. The proximal portion 118 further comprises a lynch pin guide 126. The lynch pin guide 126 penetrates the proximal portion 118 from the medial side 120 through the lateral side 122. The lynch pin guide 126 is anatomically oriented to accept a K-wire positioned perpendicular to a long axis of the fifth metatarsal that is placed to provide an axis for translation, a provisional fixation, and a mount for the osteotomy guide 100. The K-wire is placed through four cortices of fixation within the fourth and fifth metatarsals. The lynch pin guide 126 is cylindrical in shape and canulated and sized to accept a 0.045 a 0.062 inch diameter K-wire, although it can be sized to accept larger or smaller diameters as needed depending on the size of the patient.

The extension portion 116 is typically straight and approximately between 40-50 mm in length, although it may be customized to fit the exact specifications/measurements of the patient's fifth metatarsal. The extension portion 116 is oriented perpendicular to the lynch pin guide 126. The intersecting wire guide 114 is also oriented perpendicular to the lynch pin guide 126 so that when the K-wires are in position through both the intersecting wire guide 114 and the lynch pin guide 126, the K-wires will intersect at 90 degrees.

The burr collar component 130 comprises a nesting portion 132 and a burr guide extension 140. The nesting portion 132 may comprise a medial side collar 134 and a lateral side collar 136. The medical side collar 134 is configured to accept the nesting portion 124 of the lateral side 122 of the proximal portion 118 of the first arm 110. Once snapped or pushed into position, the medial side collar 134 allows the burr collar component 130 to rotate with respect to the first arm 110 as described infra. Alternatively, the nesting portion 132 may be configured without collars in any other form that would allow the burr collar component 130 to nest with the first and second arms 110 and 150.

The nesting portion 132 of the burr collar component 130 further comprises a lynch pin guide 138. The lynch pin guide 138 of the burr collar component 130 is sized and oriented to align with the lynch pin guide 126 of the first arm 110 to accept passage of a K-wire. The lynch pin guide 138 penetrates the nesting portion 132 from the medial side collar 134 through the lateral side collar 136. The lynch pin guide 138 of the burr collar component 130 is anatomically oriented to accept a K-wire positioned perpendicular to a long axis of the fifth metatarsal that is placed and extends through the lynch pin guide 126 of the first arm 110. The lynch pin guide 138 is similarly cylindrical in shape and canulated and sized to accept a 0.045 a 0.062 inch diameter K-wire, although it can be sized to accept larger or smaller diameters as needed depending on the size of the patient.

The burr guide extension 140 extends from the nesting portion 132 and comprises a burr opening 142. The burr opening is cylindrical in shape and canulated and sized to accept a burr for performing an osteotomy parallel with and medial to the K-wire positioned perpendicular to a long axis of the fifth metatarsal. Once the osteotomy is performed, the burr guide extension 140 is rotatable around the nesting portion of the proximal portion 118 of the first arm 110 to reposition the burr guide extension 140 distally.

The second arm 150 comprises a distal portion 152, an extension portion 162, and a proximal portion 164. When the osteotomy guide 100 is assembled, the first arm 110 and the second arm 150 extend in opposing directions. The distal portion 152 comprises a medial side 154 and a lateral side 158. The medial side 154 comprises a nesting portion 156. The nesting portion 156 is configured to engage the lateral side collar 136 of the nesting portion 132 of the burr collar 130 Once snapped or pushed into position, the lateral side collar 136 allows the burr collar component 130 to rotate with respect to the second arm 150. As such, the burr collar component 130 can rotate freely with respect with respect to the first and second arms 110 and 150 when sandwiched between.

The distal portion 152 further comprises a lynch pin guide 160. The lynch pin guide 160 penetrates distal portion 152 from the medial side 154 through the lateral side 158. The lynch pin guide 160 is anatomically oriented to accept a K-wire positioned perpendicular to a long axis of the fifth metatarsal that is placed and extends through the lynch pin guide 126 of the first arm 110 and the lynch pin guide 138 of the burr collar component 130. The lynch pin guide 160 is similarly cylindrical in shape and canulated and sized to accept a 0.045 a 0.062 inch diameter K-wire, although it can be sized to accept larger or smaller diameters as needed depending on the size of the patient. The lynch pin guide 160 of the second arm 150 is sized and oriented to align with the lynch pin guides 126 and 138 of the first arm 110 and the burr collar component 130 to accept passage of a K-wire.

The proximal portion 164 forms a j-arm that curves out of the extension portion 164. The proximal portion 164 terminates in a throw wire guide 166. The throw wire guide 166 is angled with respect to the extension portion 162 extending back toward the distal portion 152. The throw wire guide 166 is cylindrical in shape and canulated and sized to accept passage of a K-wire or similar pin for temporary fixation. Typically, the throw wire guide 166 is sized to accept a 0.045 inch diameter K-wire, although it can be sized to accept larger or smaller diameters as needed depending on the size of the patient. When the second arm 150 is in position, the throw wire guide 166 is anatomically oriented to position a K-wire that converges at an angle on a point of intersection of the K-wire positioned perpendicular to a long axis of the fifth metatarsal and the K-wire positioned parallel to a long axis of the fifth metatarsal. The angle of convergence is approximately oriented at 80 degrees with respect to the lynch pin guide 160 of the second arm 150, although the angle of convergence may vary up to ten degrees in either direction to accommodate different anatomy, as necessary.

The extension portion 162 is typically straight and approximately between 50-70 mm in length, although it may be customized to fit the exact specifications/measurements of the patient's fifth metatarsal. The extension portion 162 is oriented perpendicular or at a slight angle to the lynch pin guide 160. When the osteotomy guide 100 is fully assembled, the first arm 110 and the second arm 150 extend in opposing directions.

Figure 4:
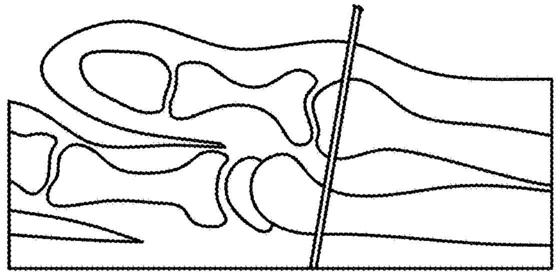
FIG. 4 illustrates a perspective side view of a lynch pin placed prior to positioning the osteotomy jig for a surgical repair of a Tailor's bunion in accordance with the disclosed architecture.

FIGS. 4-16 illustrate an exemplary procedure and method of a surgical repair of a Tailor's bunion using the osteotomy guide 100. FIG. 4 illustrates a first step comprising an insertion of an initial lynch pin K-wire that provides an axis for translation, provisional fixation, and a mount for the osteotomy guide 100. The lynch pin K-wire is inserted through the heads of the $5^{th}$ and $4^{th}$ metatarsals perpendicular to a long axis of the $5^{th}$ metatarsal, ideally bisecting the $5^{th}$ metatarsal head. This provides four cortices of provisional fixation.

Figure 5:
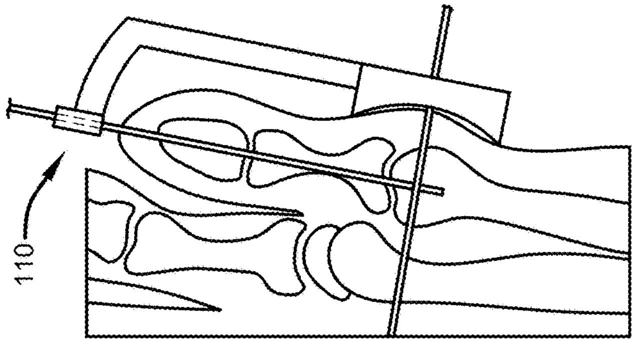
FIG. 5 illustrates a perspective side view of a first arm of the osteotomy jig of the present invention for a surgical repair of a Tailor's bunion in accordance with the disclosed architecture.

FIG. 5 illustrates a second step where the lynch pin guide 126 of the proximal portion 118 of the first arm 110 is positioned around initial lynch pin K-wire with the distal portion 112 directed distally. Next, an intersecting K-wire is placed through the intersecting wire guide 114 parallel to a long-axis of the $5^{th}$ metatarsal to allow a uniform translation of the $5^{th}$ MPJ.

Figure 6:
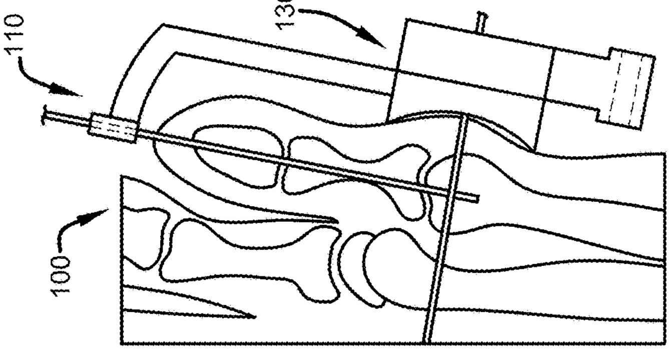
FIG. 6 illustrates a perspective side view of the first arm and a burr collar component of the osteotomy jig of the present invention for a surgical repair of a Tailor's bunion in accordance with the disclosed architecture.
Figure 7:
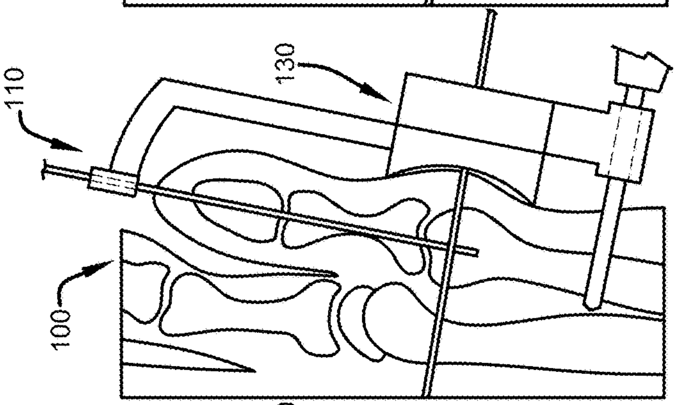
FIG. 7 illustrates a perspective side view of the first arm and the burr collar component of the osteotomy jig of the present invention for a surgical repair of a Tailor's bunion in accordance with the disclosed architecture.
Figure 8:
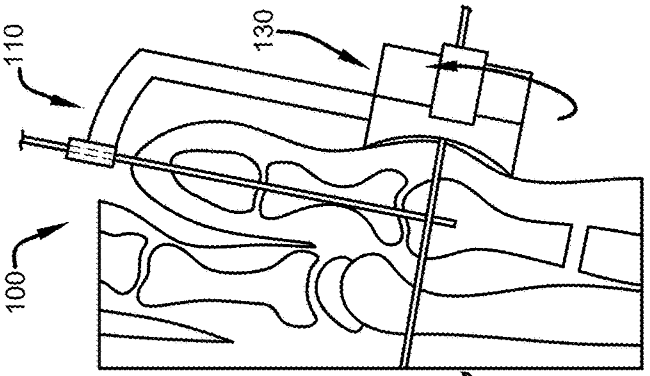
FIG. 8 illustrates a perspective side view of the first arm and the burr collar component of the osteotomy jig of the present invention for a surgical repair of a Tailor's bunion in accordance with the disclosed architecture.
Figure 10:
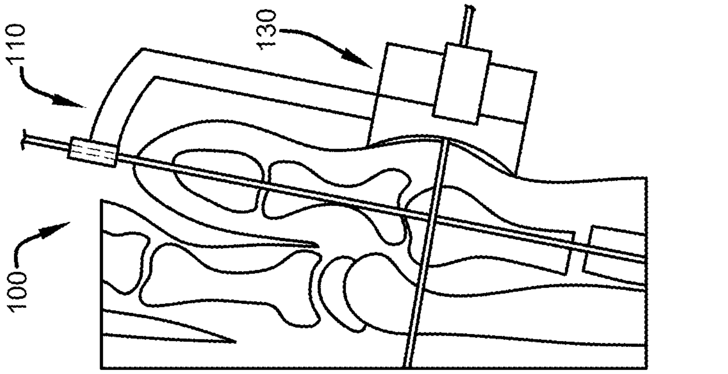
FIG. 10 illustrates a perspective side view of the first arm and the burr collar component of the osteotomy jig of the present invention for a surgical repair of a Tailor's bunion in accordance with the disclosed architecture.
Figure 9:
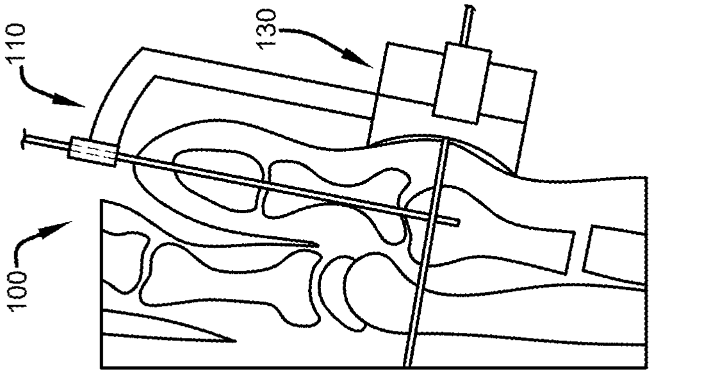
FIG. 9 illustrates a perspective side view of the first arm and the burr collar component of the osteotomy jig of the present invention for a surgical repair of a Tailor's bunion in accordance with the disclosed architecture.

FIG. 6 illustrates a third step where the lynch pin guide 138 of the burr collar component 130 is positioned around the initial lynch pin K-wire and nested into the first arm 110. Then a burr is guided through the burr opening 142 and a MIS osteotomy cut is performed through the $5^{th}$ metatarsal parallel and medial to the axis guide created by the initial lynch pin K-wire as illustrated in FIG. 7. The burr guide extension 140 is then rotated upward out of the way at step five and the portion of the $5^{th}$ metatarsal is translated medially to achieve a proper anatomical orientation as illustrated in FIGS. 8-10.

Figure 12:
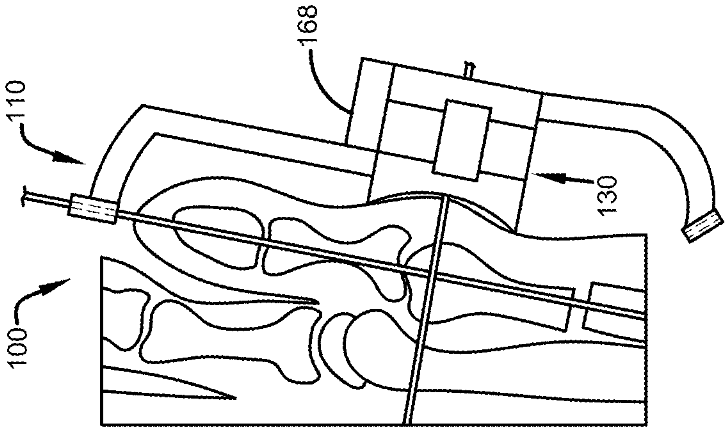
FIG. 12 illustrates a perspective side view of the first arm, the burr collar component, and a second arm of the osteotomy jig of the present invention for a surgical repair of a Tailor's bunion in accordance with the disclosed architecture.
Figure 11:
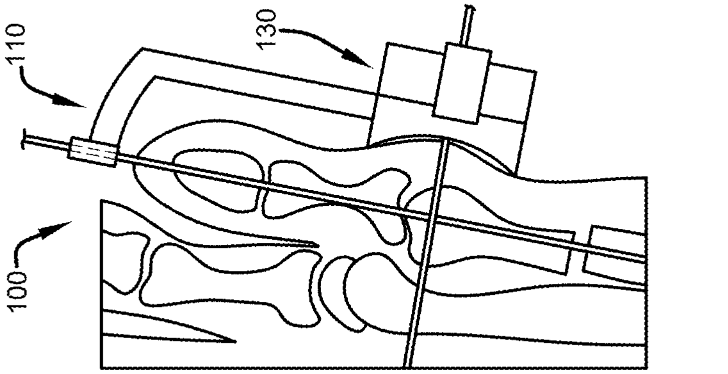
FIG. 11 illustrates a perspective side view of the first arm and the burr collar component of the osteotomy jig of the present invention for a surgical repair of a Tailor's bunion in accordance with the disclosed architecture.

FIG. 11 illustrates a sixth step where the intersecting K-wire is advanced medially past the osteotomy site to provide temporary fixation maintaining translation. FIG. 12 illustrates a seventh step of positioning the second arm 150 around lynch pin K-wire so that the second arm 150 is nested with the burr collar component 130. Once positioned, the throw wire guide 166 of the second arm 150 is oriented to position a throw wire K-wire that will be slaved to the intersection of the lynch pin and the intersecting K-wires.

Figure 13:
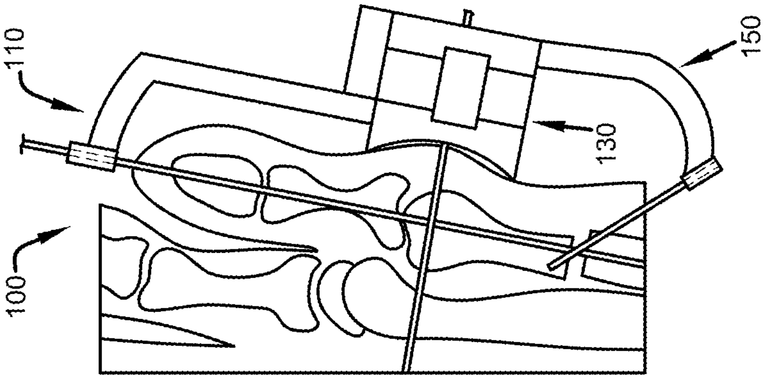
FIG. 13 illustrates a perspective side view of the first arm, the burr collar component, and the second arm of the osteotomy jig of the present invention for a surgical repair of a Tailor's bunion in accordance with the disclosed architecture.
Figure 14:
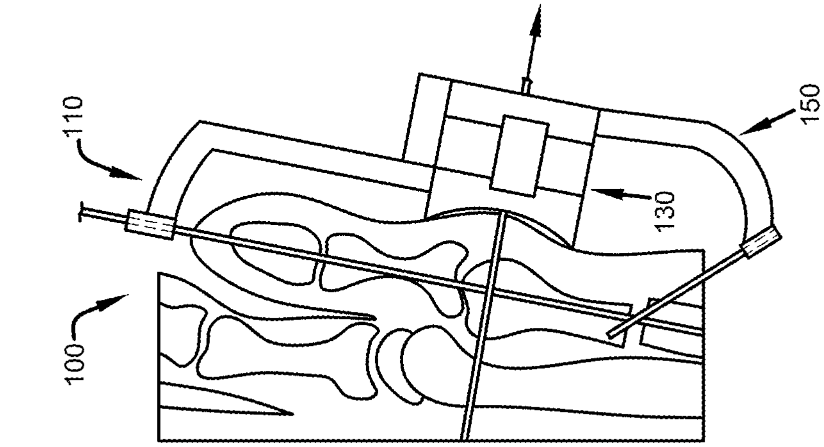
FIG. 14 illustrates a perspective side view of the osteotomy jig of the first arm, the burr collar component, and the second arm of the osteotomy jig of the present invention for a surgical repair of a Tailor's bunion in accordance with the disclosed architecture.
Figure 15:
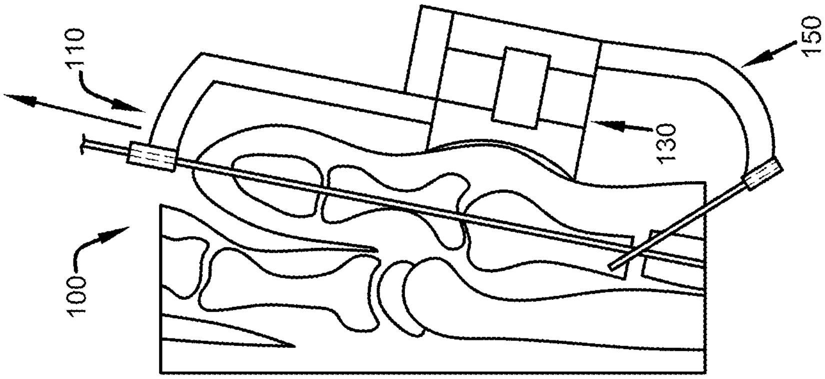
FIG. 15 illustrates a perspective side view of the first arm, the burr collar component, and the second arm of the osteotomy jig of the present invention for a surgical repair of a Tailor's bunion in accordance with the disclosed architecture.
Figure 16:
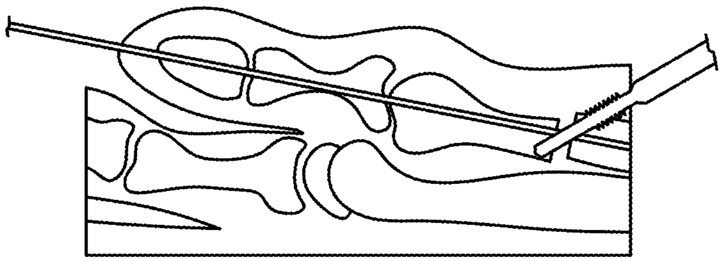
FIG. 16 illustrates a perspective side view of a permanent fixation screw placed after removing the osteotomy jig for a surgical repair of a Tailor's bunion in accordance with the disclosed architecture.

FIG. 13 illustrates an eighth step of placing the throw K-wire through the throw wire guide 166 for additional fixation in a third direction. FIG. 14 illustrates a ninth step of removing the lynch pin wire, and FIG. 15 illustrates the tenth step of disassembling the osteotomy jig 100. FIG. 16 illustrates an eleventh step of finishing the procedure by placing a bone screw for permanent fixation of the repaired Tailor's bunion.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An osteotomy jig for a surgical repair of a Tailor's bunion comprising:

a first arm comprising a distal portion, an extension portion, and a proximal portion;

a burr collar component comprising a nesting portion and a burr guide extension; and a second arm comprising a distal portion, an extension portion, and a proximal portion; and wherein the proximal portion of the first arm and the distal portion of the second arm are each configured to nest within opposing sides of the nesting portion of the burr collar component; and wherein the first and second arms are j-arms.

2. The osteotomy jig of claim 1, wherein the first arm and the second arm extend in opposing directions.

3. The osteotomy jig of claim 1, wherein the distal portion of the first arm comprises an intersecting wire guide.

4. The osteotomy jig of claim 1, wherein the proximal portion of the first arm comprises a lynch pin guide.

5. The osteotomy jig of claim 1, wherein the proximal portion of the first arm comprises a cupped medial side.

6. The osteotomy jig of claim 1, wherein the nesting portion of the burr collar component comprises a medial side collar and a lateral side collar.

7. The osteotomy jig of claim 6, wherein a nesting portion of a lateral side of the proximal portion of the first arm nests within the medial side collar of the burr collar component.

8. The osteotomy jig of claim 6, wherein a nesting portion of a medial side of the distal portion of the second arm nests within the lateral side collar of the burr collar component.

9. The osteotomy jig of claim 6, wherein the burr collar component is rotatable between the first and second arms.

10. The osteotomy jig of claim 6, wherein the burr guide extension comprises a burr opening.

11. The osteotomy jig of claim 1, wherein the distal portion of the second arm comprises a lynch pin guide.

12. The osteotomy jig of claim 1, wherein the proximal portion of the second arm comprises a throw wire guide.

13. An osteotomy jig for a surgical repair of a Tailor's bunion comprising:

a first arm comprising a distal portion comprising an intersecting wire guide, an extension portion, and a proximal portion comprising a lynch pin guide;

a burr collar component comprising a nesting portion comprising a lynch pin guide, and a burr guide extension comprising a burr opening; and a second arm comprising a distal portion comprising a comprising a lynch pin guide, an extension portion, and a proximal portion comprising a throw wire guide; and wherein the proximal portion of the first arm and the distal portion of the second arm are each configured to nest within the nesting portion of the burr collar component.

14. The osteotomy jig of claim 13, wherein the intersecting wire guide and the throw wire guide are each sized to accept a 0.045 inch diameter K-wire.

15. The osteotomy jig of claim 13, wherein the lynch pin guides are each sized to accept a 0.062 inch diameter K-wire.

16. The osteotomy jig of claim 13, wherein the lynch pin guide of the first arm is oriented perpendicular to the extension portion of the first arm.

17. The osteotomy jig of claim 13, wherein the intersecting wire guide of the first arm is oriented perpendicular to the lynch pin guide of the first arm.

18. The osteotomy jig of claim 13, wherein the throw wire guide is oriented at 80 degrees with respect to the lynch pin guide of the second arm.

19. An osteotomy jig for a surgical repair of a Tailor's bunion comprising:

a first j-arm comprising a distal portion comprising an intersecting wire guide, an extension portion, and a proximal portion comprising a lynch pin guide oriented perpendicular to the intersecting wire guide;

a burr collar component comprising a nesting portion comprising a lynch pin guide, and a burr guide extension comprising a burr opening; and a second j-arm comprising a distal portion comprising a lynch pin guide, an extension portion, and a proximal portion comprising a throw wire guide; and wherein the proximal portion of the first j-arm and the distal portion of the second j-arm are each configured to nest within the nesting portion of the burr collar component; and wherein the lynch pin guides of the first j-arm, the burr collar component, and the second j-arm are all configured to accept a K-wire within.

* * * * *